United States Patent [19]
Gergely et al.

[11] Patent Number: 4,678,661
[45] Date of Patent: Jul. 7, 1987

[54] EFFERVESCENT COMPOSITION AND METHOD OF MAKING SAME

[76] Inventors: Gerhard Gergely; Thomas Gergely; Irmgard Gergely, all of Gartengasse 8, A1050 Wein, Austria

[21] Appl. No.: 880,081

[22] Filed: Jun. 30, 1986

Related U.S. Application Data

[63] Continuation-in-part of Ser. No. 655,919, Sep. 27, 1984, abandoned.

[30] Foreign Application Priority Data

Sep. 28, 1983 [AT] Austria ................................. 3450/83
Sep. 21, 1984 [DE] Fed. Rep. of Germany ....... 3434774
May 21, 1986 [DE] Fed. Rep. of Germany ....... 3617058

[51] Int. Cl.$^4$ ............................................. A61K 33/10
[52] U.S. Cl. .................................... 424/44; 424/156; 424/466; 514/819; 514/474
[58] Field of Search ....................... 424/16, 43, 44, 53, 424/156; 514/165, 819, 820, 474; 252/90, 91

[56] References Cited

U.S. PATENT DOCUMENTS

| | | | |
|---|---|---|---|
| 3,495,001 | 2/1970 | Leonards | 424/44 |
| 3,556,803 | 1/1971 | Ehrreich et al. | 424/44 |
| 3,594,472 | 7/1971 | Sopp et al. | 514/165 |
| 3,773,922 | 11/1973 | Gergely | 424/44 |
| 4,083,951 | 4/1978 | Goudie et al. | 424/44 |
| 4,093,710 | 6/1978 | Sass et al. | 424/44 |
| 4,256,599 | 3/1981 | Krisp et al. | 424/53 |
| 4,294,819 | 10/1981 | Tencza | 424/16 |
| 4,339,428 | 7/1982 | Tencza | 424/16 |
| 4,417,993 | 11/1983 | Gergely | 252/90 |
| 4,446,135 | 5/1984 | Fountaine | 424/157 |

FOREIGN PATENT DOCUMENTS 749864 10/1970 Belgium ................................ 424/44

Primary Examiner—Ronald W. Griffin
Attorney, Agent, or Firm—Hill, Van Santen, Steadman & Simpson

[57] ABSTRACT

Effervescent granulates, particularly for the manufacture of effervescent tablets, comprising at least one solid, crystalline edible organic acid and at least one carbonate which releases carbon dioxide upon reaction with the organic acid, the acid crystals comprising a coating which contains calcium carbonate adhering to the surface of the acid crystals by means of a bonding layer formed by a reaction at the interface with the crystal of a calcium carbonate coating material. The coating is built up in multi-layers and includes at least two carbonate layers, the layer which is bonded essentially to the acid crystal being composed of calcium carbonate with the succeeding layers adhering to the carbonate layer by means of a bonding layer formed by reaction of the acid and the carbonate. The invention also deals with methods of manufacture as well as fields of use for the new effervescent granulates.

32 Claims, No Drawings

EFFERVESCENT COMPOSITION AND METHOD OF MAKING SAME

CROSS-REFERENCE TO RELATED APPLICATION

This application is a continuation-in-part of the application of Gerhard Gergely, Ser. No. 655,919, filed Sept. 27, 1984, now abandoned.

BACKGROUND OF THE INVENTION

1. Field of the Invention

The present invention is in the field of effervescent granulates containing an edible organic acid coated with a calcium carbonate-containing layer, the two being bonded at the interface by means of a reaction product between the acid and the carbonate.

2. Description of the Prior Art

Effervescent tablets are usually based on the reaction of an organic acid such as citric acid, tartaric acid, and a substance which liberates $CO_2$, such as sodium bicarbonate, sodium carbonate, potassium bicarbonate or potassium carbonate. There have been frequent criticisms that such systems have an excessively high proportion of sodium ions and it would be desirable to provide an effervescent system in which fewer or possibly no sodium ions were contained. The utilization of potassium bicarbonate and potassium carbonate alone fails to meet the need because, first, the potassium compounds give the substance an unpleasant soapy taste, and second, the moisture sensitivity due to the introduction of potassium salts leads to great technical problems.

It would be desirable to employ carbon dioxide liberating agents such as calcium carbonate and magnesium carbonate. Calcium carbonate would be preferred but it cannot be employed without difficulty because it reacts extremely slowly with an organic acid and therefore effervescent systems containing calcium carbonate require far too long to dissolve.

European OS No. 0 076 340 discloses an effervescent granulate as well as a method wherein, using citric acid as the organic acid, the acid crystals are provided with a single-layer coating which contains calcium carbonate. Such effervescent granulates or effervescent mixtures have definitely proven themselves whether used as instant mixes for producing effervescent beverages or employed in the manufacture of effervescent tablets. Still, it is desirable to further increase the calcium content of such effervescent granulates. This has proven difficult because calcium carbonate reacts extremely slowly with organic acids and effervescent systems which rely solely on such sources of calcium carbonate take a long time to dissolve.

What is especially desirable is an improvement of the known effervescent granulate as well as a method for the manufacture thereof to provide further improvement in the storage properties, and an increase in the calcium concentration together with simultaneous enhancement of the solubility in water.

SUMMARY OF THE INVENTION

In accordance with the present invention, there is provided an effervescent granulate including a core of solid, edible organic acid crystals with a layer of calcium carbonate bonded to the core by means of a reaction product bonding layer produced by a reaction at the interface between the core and the layer of calcium carbonate. A second layer of a carbonate or bicarbonate envelops the first layer either by attaching itself to the voids left in the initial coating of calcium carbonate, or through the interposition of another layer of organic acid which bonds itself to the initially deposited calcium carbonate as well as to the subsequently deposited carbonate layer.

In one of the features of the present invention, one of the layers also contains sodium or potassium bicarbonate or both.

The original bonding layer should cover at least 80% of the surface of the organic acid crystals, and preferably at least 95% thereof. The grain size of the calcium carbonate is usually about one order of magnitude smaller than that of the organic crystals. For the best effectiveness, the bonding layer adjacent to the calcium carbonate layer should contain a maximum of about 5% by weight of calcium carbonate and preferably should not exceed about 2% by weight. Generally, the calcium carbonate has a particle size not in excess of about 20 microns.

The method for the manufacture of the effervescent granulate of the present invention comprises moistening particles of a crystalline edible organic acid with a solvent for the acid, and then mixing the moistened acid particles under agitation with solid, powdery calcium carbonate under conditions sufficient to produce a surface reaction between the crystals and the calcium carbonate. This results in the formation of a generated calcium carbonate layer upon the crystals with the elimination of reaction water. Then, additional crystalline organic acid may be added with agitation to react with the generated calcium carbonate layer while the same is still damp with the water resulting from the initial reaction. Then, calcium carbonate or an alkali bicarbonate are added to the particles thus treated to react with the remaining additional crystalline organic acid, the steps of adding crystalline organic acid and calcium carbonate or alkali bicarbonate being repeated until the desired number of additional layers has been built up. Finally, a vacuum is applied to terminate further layer formation.

DESCRIPTION OF THE PREFERRED EMBODIMENTS

The present invention is based in part upon the discovery that the unsatisfactory properties of previous effervescent granulates can be substantially eliminated by providing at least two layers containing calcium carbonate. In the present invention, therefore, after the calcium carbonate has been applied to the acid crystals and adhered thereto by a surface reaction, this initial coating is followed by the deposition of further carbonate layers. At least one further calcium carbonate layer adheres to the first calcium carbonate layer bonded to the acid crystal by reacting thereto via a bonding layer formed by reaction therewith. This occurs because water which is released by the neutralization reaction when the calcium carbonate layer reacts with the acid crystal layer beneath it is capable of being used, in turn, for the reaction of the succeeding carbonate layer. This is facilitated in that the bonding layer does not itself entirely cover the acid crystal but only partially covers it so that further layers can still enter into reaction with the acid crystal through the void spaces.

As a result of the multi-layer structure, an unexpectedly rapid reaction between the acid such as citric acid and calcium carbonate, including calcium carbonate in high concentrations, occurs which reaction would otherwise proceed far more slowly. Due to the extensive covering of the acid crystals, moreover, a reliable passivation thereof with respect to ambient moisture is also achieved. One of the advantages which results from this feature is that no foreign bonding agents whatever need be used for constructing the system, i.e., the adhesion of the components is achieved solely by means of the bonding layer.

In accordance with the present invention, the grain size of the calcium carbonate is preferably around one order of magnitude lower than that of the acid crystals which results in an optimum coherent coating on the acid crystals. When the bonding layer is composed of a maximum of 5% by weight, preferably a maximum of 2% by weight, of the calcium carbonate in the form of the acid salt, then an optimum quantity of calcium carbonate is available for the effervescent reaction. When the calcium carbonate component of the effervescent granulate has a maximum particle size of 20 microns, then the reaction surface of the calcium carbonate is so great that a reaction rate comparable to that achieved with sodium carbonate is achieved.

Since the bonding layer in the effervescent mixture of the present invention substitutes for a bonding agent which is usually employed in powder technology, there is also the possibility of using this bonding layer for the agglomeration of mineral substances and/or vitamins. The invention further provides for the use of such effervescent tablets for the mineralization of soft drinks. This is especially appropriate because there is a depletion of essential minerals from the use of soft drinks that are extremely highly sweetened with sugar, are decidedly low in mineral salts, and may contain excessive amounts of sodium chloride. Since the effervescent materials of the present invention have a complete lack or extremely low content of sodium ions, the tablets of the invention permit great quantities of calcium, magnesium, potassium, and other essential ions to be palatably introduced into a soft drink.

The employment of the effervescent granulate of the present invention permits the manufacture of an effervescent tablet including a coating free of sodium ions which is composed of a first layer containing sodium carbonate, a second layer containing potassium bicarbonate, and a third layer containing fumaric acid which also contains some acetylsalicylic acid. The effervescent tablet manufactured in accordance with the invention can also have a plurality of layers, preferably two layers, which differ in composition. One of the tablet layers may be free of effervescent mixture and contain at least one other active ingredient. For example, one of the tablet layers can contain paracetamol and one of the tablet layers can contain acetylsalicylic acid.

It has been found that the effervescent reaction between organic acid such as citric acid and calcium carbonate can be accelerated if the acid crystals are coated with calcium carbonate and thereby create intimate contact between the calcium carbonate and the citric acid at the surface of the crystals. The reaction speed between acid and carbonate is comparable to the reaction between carbonates or bicarbonates of the alkalies. As previously mentioned, it is desirable to use a bonding agent which is the reaction product of about 5 to 10% of the calcium carbonate to the surface of the acid such as citric acid which results in the formation of the calcium salt corresponding to the acid. The surface reaction between the calcium carbonate and the acid serves the purpose of firmly anchoring the calcium carbonate to the surface of the acid so that no separation of the structure can occur even during later mixing. The bonding mechanism is achieved by using citric acid crystals of various sizes, for example, from 50 microns to 500 microns and moistening them with a mixture of alcohol and water. The pressure is then reduced down to about 500 mbar as, for example, in a vacuum mixer. The calcium carbonate is then drawn in and with a 500 mbar vacuum, mixing is begun with an agitator which preferably vibrates around its horizontal axis and agitates opposite to the force of gravity. As a result of this three-dimensional mixing motion, all the pre-moistened citric acid crystals are brought into contact with calcium carbonate. The resulting reaction can be measured in terms of the drop in the extent of vacuum which occurs. The mono-calcium citrate layer produced serves as a bonding agent for the calcium carbonate sticking to the surface due to the moisture. The system remains mechanically and chemically stable due to the elimination of moisture which is carried out. Quantities of calcium carbonate which roughly correspond to the stoichiometric quantity of 1 mol citric acid to 1 mol calcium carbonate are introduced in this way, whereby only 5 to 10% of the calcium carbonate mols are brought to reaction.

Manufacture under vacuum conditions permits a precise control and an exact termination of the reaction at any point in time as well as an exact reproducibility of the method. A correspondingly slow rate of agitation leads to a continuous progress of the reaction, but not to a destruction thereof as would be the case, for example, in fluidized solids drying. Of particular importance when manufacturing under vacuum is that the finished sodium-free or low-sodium effervescent tablet dissolves very rapidly, as fast as a traditional tablet based on sodium bicarbonate and, moreover, is significantly less sensitive to moisture.

In another embodiment of the present invention, at least one layer containing calcium carbonate also includes calcium gluconate. It is especially important that the calcium gluconate be present in anhydrous form since it can thereby serve as an additional drying agent. Thus, when the coating layer containing the calcium carbonate dissolves, a substantial turbulence occurs in the effervescent beverage since it is water-insoluble in and of itself.

The system of the present invention may employ controlled quantities of potassium bicarbonate or potassium carbonate together with a slight quantity of sodium carbonate, depending on whether the product is to be designated "low sodium" or "very low sodium". In selecting the organic acids, those acids should be used which do not produce insoluble calcium salts. Consequently, acids such as malic acid, fumaric acid, adipic acid, and the like, are employable together with the preferred citric acid. It is obvious that the effervescent tablet of the invention can contain further standard additives such, for example, as inert fillers such as mannitol or the like. Methods and apparatus which are especially suited for the manufacture of the effervescent systems of the invention are disclosed in AT Pat. No. 376 147.

In another embodiment of the present invention, synergistically acting, water-free starch as well as water-free, water-insoluble calcium salts may be used as additives. Suprisingly, the improved granulates of the present invention can incorporate such materials without deteriorating the rate of dissolution and in fact may even increase the rate. The additives provide a noticeable improvement of the keeping qualities of the tablet since not only calcium carbonate is employed, but in at least one of the coating layers containing calcium carbonate there may be water-free starch and water-free calcium salts added to it. Since these additives are employed free of water, they themselves act as additional drying agents during storage of the tablets and prevent chain reactions which release water from being initiated between the citric acid and the calcium carbonate. These chain reactions would lead to a premature aging and deterioration of the effervescent granulate or of the effervescent tablet. Further, the starch acts as a dispersant for the additional calcium salts which are otherwise water insoluble so that these are distributed especially quickly in the water when the effervescent tablet is dissolved. Effervescent granulates manufactured in accordance with the present invention are particularly suitable as instant preparations, whereby the dissolving time amounts to only about 20 to 30 seconds at 5° C. in comparison to known calcium carbonate preparations which may require several minutes dissolving time at such low temperatures. It is important that both the starch as well as the water-insoluble calcium salts be incorporated into the coating layer produced during granulation in a vacuum since the mechanical explosive-like effect produced in accordance with the invention by the synergistic action of the starch with the water-insoluble calcium salts would not otherwise occur. Effervescent granulates manufactured in accordance with the present invention keep so well that due to the drying properties of the water-free starch and of the water-insoluble, water-free calcium salts, the granulates can be practically stored in an open bottle.

The invention will be set forth in more detail with reference to various examples.

EXAMPLE 1

A mixture of 22 parts citric acid having a grain size between 0.4 and 0.6 mm and 43 parts citric acid of a grain size of about 0.1 mm were mixed, heated to 40° C., and mixed with 10 parts of a 50% ethanol solution. After five minutes of oscillating mixture, evacuation to 500 mbar was carried out and 20 parts of micronized calcium carbonate were introduced. Without agitation, evacuation was carried out again and when the pressure reached 500 mbar, mixing was carried out in an oscillating fashion and the valve to the vacuum pump was turned off. The resulting reaction permitted the pressure to rise slowly, and upon attaining a vacuum of 200 mbar pressure, full vacuum was applied. The difference in the overlying space pursuant to calculation of the pressure difference yields a conversion of approximately 4% of the quantity of calcium carbonate to monocalcium citrate.

After the pressure had reached 800 mbar, the agitation was suspended and drying was carried out to a pressure of 10 mbar under occasional agitation. Up to 80 parts potassium bicarbonate and up to 30 parts sodium bicarbonate could then be mixed into this system. However. the system by itself also provides usable effervescent tablets.

The base produced according to this example is particularly suited in the manufacture of highly dosed acetylsalicylic acid effervescent tablets which have a lower quantity of alkaline and alkaline earth ions whereas up to the present time a very large quantity of sodium ions was necessary for the effervescent effect.

EXAMPLE 2

An amount of 22 parts of citric acid having a particle size of about 0.5 mm were mixed with 88 parts of citric acid having a particle size of 0.1 mm and moistened with 20 parts of an ethanol-water solution. An amount of 22 parts of calcium carbonate were introduced and, after drying, 60 parts of potassium bicarbonate and 10 parts sodium bicarbonate were added.

Up to 40 parts of lactose can also be introduced, depending upon the desired acetylsalicylic acid concentration, the corresponding effervescent system being diluted in order to increase the stability of the acetylsalicylic acid. According to this composition, effervescent tablets of 4 g can be manufactured which contain up to 1 g acetylsalicylic acid in individual dosage form.

EXAMPLE 3

About 40 parts citric acid having a grain size of 0.7 mm were mixed with 30 parts ascorbic acid and an additional 45 parts of pulverized citric acid. Moistening was again carried out with 25 parts of a mixture of 70% ethanol and 30% water, and a reaction was carried out with 25 parts calcium carbonate as in Example 1. After drying to 10 mbar, 80 parts of potassium bicarbonate and 60 parts lactose of a grain size of 0.2 mm were added and the mixture was compressed into tablets. The low sodium vitamin C effervescent tablets have approximately the same rate of dissolution as those which were manufactured with sodium bicarbonate.

EXAMPLE 4

About 22 parts by weight of citric acid having a grain size between 0.3 and 0.6 mm and 30 parts by weight citric acid having a grain size of 0.1 mm were mixed, heated to 40° C., and compounded with a solution containing 13 parts by weight gluconic acid-delta-lactone in 5 parts by weight water. Reaction was carried out as in Example 1 and drying was carried out as in the same Example.

The addition of the gluconic acid-delta-lactone whereby 1 part by weight of the lactone is converted into gluconic acid has the advantage that the dissolution rate of the system is accelerated and that reaction-retarding surface bufferings are prevented due to the different pH of the citric acid and of the gluconic acid.

EXAMPLE 5

About 20 parts crystallized citric acid were moistened in a vacuum mixer with 5 parts ethanol and 5 parts water and heated to 60° C. Then, 30 parts of calcium carbonate were added and the mixture was allowed to react. The first evacuation was carried out to approximately 100 mbar, and the empty space in the vacuum mixer was allowed to fill with $CO_2$ gas from the reaction to a pressure of 900 mbar. The gas development was repeated a second time and then stopped through the application of vacuum. Subsequently, 10 parts of potassium bicarbonate were added and an additional 20 parts citric acid were added, and passivation was repeated with two parts ethanol and one part water. In this manner, a passivated effervescent mixture resulted which consists of surface reacted calcium carbonate and potassium bicarbonate, and possesses a marked stability against humidity.

The basic effervescent mixture can be combined with sodium bicarbonate in an amount permitted legally for low sodium mixtures. Together with a conventional multivitamin mixture, this mixture yields a readily compressible effervescent tablet mixture with an extremely low concentration of sodium ions.

EXAMPLE 6

About 105 parts ascorbic acid (vitamin C) and 130 parts citric acid were heated with 6 parts ethanol and 3 parts water to 60° C. and treated with 22 parts calcium carbonate as in Example 1. In this case, the ascorbic acid also evidences a surface reaction with calcium carbonate to increase the stability of the system in an exceptional fashion. The ascorbic acid with its low pH and its ready water solubility is passivated on the surface and thereby rendered less prone to reaction.

Subsequently, 10 parts potassium bicarbonate and 10 parts of citric acid are added so that all free surface locations on the acids have been passivated with calcium or potassium salts through surface reaction. In this instance, also, toward the end drying was carried out to a value of at least 20 mbar and then flavorings and dyes can be added dry and compressed.

EXAMPLE 7

The manufacture of low sodium salicylic acid containing effervescent tablets presents a certain amount of difficulty. For example, 68 parts citric acid were moistened with two parts ethanol and one part water, heated to 60° C. and brought to reaction with 20 parts of calcium carbonate. Immediately thereafter, 40 parts of potassium bicarbonate were allowed to react for only one time by introducing two parts of 70% ethanol for the start of the reaction. After the partial drying, 20 parts of fumaric acid were added in micronized form in order to coat the possibly still-open locations of the reaction products with fumaric acid. This can be accomplished in a particularly satisfactory manner by drying off the preceding reactions only to a specific vacuum value, for example, 90 mbar, so that a low residual moisture content remains which keeps the micronized fumaric acid on the surface.

This mixture can be combined in the ratio of up to 2:1 with salicylic acid and yields hard, rapidly disintegrating effervescent tablets which contain no sodium ions and are distinguished by a minimum saponification of the free salicylic acid even in the case of longer storage.

In order to improve the disintegration rate, depending on the respective specifications, minor quantities of sodium bicarbonate can be added. Also, a dilution or extending of the effervescent tablet with inert substances such as mannitol is possible, whereby more rapid disintegration times and improved stabilities result. A ratio of mannitol to effervescent mixture in the amount of 1:1 still provides rapidly disintegrating and stable effervescent systems.

EXAMPLE 8

More complex effervescent tablets can be manufactured in accordance with the method of this invention, this technique being particularly expedient when it is a matter of bringing together incompatible substances. For example, it is possible to unite the incompatible system of paracetamol/acetylsalicylic acid in a two-layer tablet in the following manner.

About 68 parts citric acid with 2 parts ethanol, moistened with 1 part water, heated to 60° C., were caused to react with 20 parts calcium carbonate as in Example 6. Before stopping the reaction, 20 parts paracetamol were introduced and immediately accumulated at the surface due to the sticky bonding force of the calcium citrate which had arisen. Only then was the product dried in the vacuum and the reaction subsequently carried out in that 40 parts potassium bicarbonate were allowed to react once with two parts of 70% ethanol. After a partial drying at a pressure up to about 100 mbar, 20 parts fumaric acid in micronized form were added.

An effervescent paracetamol tablet can be provided by pressing in the form of a two-layer tablet the final mixture using the ratios given in Example 7 (effervescent acetylsalicylic acid tablet), whereby only about 0.8% of the acetylsalicylic acid is lost as free salicylic acid with the two-layer tablet, this being attributed to the compressed boundary layer between the two phases of the two-layer tablet.

As a consequence of the extremely good effervescent qualities of the paracetamol basic tablet, however, one can also produce a two-layer tablet where, for example, the basic mixture is produced from an effervescent tablet of 2.8 g which contains a corresponding amount of paracetamol. A second layer, an acetylsalicylic acid mixture consisting of 200 mg acetylsalicylic acid and 500 mg common lactose, can be pressed on, to produce a two-layer tablet totalling 3.5 g. Although the aspirin is present therein in a non-effervescing form, the effervescent effect of the layer containing paracetamol is sufficient in order to effect complete dissolution of the acetylsalicylic acid in the overall tablet. The extraordinary advantages of this system reside in that the paracetamol is completely stable in the low-sodium effervescent phase but saponification effects of both the paracetamol as well as the sodium-free effervescent mixture on the aspirin are suppressed. It is thus possible to produce hitherto unmanufacturable effervescent tablets with incompatible components by means of a simple two-layer tablet press, even in a low-sodium form.

EXAMPLE 9

It is also possible to manufacture sodium-free or low-sodium effervescent tablets enriched with minerals and vitamins, for example, the B complex.

500 parts of citric acid having a grain size of 0.2 to 0.3 mm were heated to 60° C. with 30 parts magnesium oxide and 150 parts calcium carbonate. A solution of 40 parts citric acid and 20 parts water was introduced and the mixture was allowed to react until the evacuated space existing thereabove, generally corresponding volume-wise to twice the parts of citric acid, had been filled with carbon dioxide. A high vacuum was then applied and drying was carried out to a value of 100 mbar. 20 parts of iron sulfate, 40 parts potassium citrate, and 10 parts of potassium chloride and a corresponding amount of the vitamin complex B1, B2 and B6 were supplied to this residually damp mixture.

The additives adhere to the residually damp but passivated basic mixture, so that a uniform, highly pourable and one that is highly resistant to atmospheric humidity is produced after the evacuation of the mass to 10–20 mbar. This material can either be employed as a granulate in packets for the production of instant sport beverages or can be pressed into effervescent tablets with the addition of 2 to 5% micronized fumaric acid.

EXAMPLE 10

70 parts of citric acid having a grain size of about 0.3 to 0.5 mm were mixed with 30 parts citric acid having a grain size of about 0.1 mm, together with 45 parts of calcium carbonate. These materials were heated to 50°

C. with occasional evacuation. As in Example 1, the valve to the vacuum pump was closed after evacuation to 500 mbar and at this time a mixture of 5 parts levulinic acid, 3 parts citric acid and 1 part lactic acid and 2 parts of water and 2 parts alcohol were slowly introduced with vibrational agitation. In this example, the overhead space of the vacuum vessel was filled twice and evacuated twice, and drying was then carried out by applying the full vacuum.

This example of formulation possibilities shows that even with increased calcium carbonate content, surface reactions, particularly dissolving in water, can delay the formation of tricalcium citrate as the final solvent product for 10 to 12 hours by employing different acids.

EXAMPLE 11

50 parts of crystalline citric acid were introduced into a preheated vacuum vessel and heated to 60° C. At this temperature, the citric acid was moistened with 5 to 10% water based upon the parts by weight of citric acid. Subsequently, 10 parts of calcium carbonate were introduced, distributed by agitation, and reacted to bond the same to the surface of the citric acid whereby further water which was uniformly distributed at the crystal surface was released by the reaction.

6 parts of powdered citric acid were then introduced, distributed at the surface of the crystals by agitation so that the citric acid could react to the layer of calcium carbonate by means of the moisture which was produced by the first reaction. An additional 10 parts of $CaCO_3$ were then introduced and reacted to the powdered citric acid layer by means of the water which had been liberated, whereby the water present in the preceding layer was absorbed, starting the new reaction, and secondarily again producing more water. The same operation occurred at the next layer which was applied with 6 parts powdered citric acid and 12 parts calcium carbonate. The water which is present and was formed by the preceding layer reaction was partly absorbed and used for the further reaction. The cessation of these reactions could be accomplished by applying a vacuum to bring the pressure down to about 10 to 20 mbar and thereby eliminate the residual moisture. It is essential, of course, that this chain reaction be terminated as quickly as possible by the application of vacuum when the desired number of layers have been built up.

It is noteworthy that the binder of the layer composed of mono-calcium citrate arises largely free of water of crystallization under these conditions, due to the higher temperatures. It should be realized that the incorporation of water of crystallization into crystallizing solutions takes place very slowly. Even this loosely bonded water of crystallization is largely eliminated at this temperature by the absorption of the next layer as well as the intermittent vacuum, so that a calcium citrate which is nearly free of water of crystallization arises as the reaction product and serves as the necessary bonding agent. With a multi-layer structure, however, this layer is also a buffer parting layer between the citric acid and calcium carbonate at the same time, thus preventing further chain reactions or greatly retarding them. The salt, free of water of crystallization which is present as the bonding agent in the multiple layer, serves as an internal drying agent in the final product since water-free calcium mono-citrate is capable of incorporating at least 1 mol water of crystallization in complex fashion and make it unavailable for chain reactions. Systems formed in this way are consequently significantly more stable than systems which are produced by single-shot application and at low temperatures and without vacuum.

With the present systems, the formation of water-free calcium citrate can be raised up to 30% of the overall quantity of calcium carbonate employed, so that the dissolving properties of the granulate can be controlled in a desired way.

EXAMPLE 12

70 parts of citric acid having a grain size of about 0.3 to 0.5 mm were mixed with 30 parts citric acid having a grain size of about 0.1 mm. The mixing was carried out in a vacuum mixer as disclosed, for example, in AT Pat. 376 147. 35 parts of calcium carbonate, 5 parts of water-free starch and 5 parts of calcium levulinate were then introduced, and heated to 50° C. under occasional evacuation and intense blending.

After evacuation to 500 mbar, the valve to the vacuum pump was closed and 20 parts micronized calcium carbonate were introduced. Without agitation, evacuation was repeated and vibrational mixing was carried out when the pressure of 500 mbar was reached. Then, the valve to the vacuum pump was again closed. The reaction which arose causes the vacuum to decay slowly and full vacuum is ultimately applied to carry out the final drying.

The effervescent granulate which is produced comprises a two-layer coating containing calcium carbonate which has reacted with the citric acid crystals, the first calcium carbonate coating layer being applied directly to the citric acid crystals and has a content of water-free starch and of water-free calcium levulinate which is well suited for instant beverages since it dissolves in about 15 seconds at 5° C. when introduced into water. The calcium concentration is significantly higher than in previously known preparations and enables the manufacture, for example, of effervescent calcium tablets having a calcium content of 1200 mg without having to increase the acid content in a manner which would have a negative effect on the use of the product or on the taste.

The features of the present invention disclosed in the above can be used both individually as well as in combination for realizing the benefits of the present invention in its various embodiments.

We claim as our invention:

1. An effervescent granulate comprising:
   a core of solid, edible organic acid crystals,
   a first layer of calcium carbonate bonded to said core by means of a reaction product bonding layer produced by a reaction at the interface between said core and said first layer of calcium carbonate, and
   a second layer of a carbonate or bicarbonate enveloping said first layer.

2. An effervescent granulate according to claim 1 which includes:
   a layer of organic acid between said first and second layers and being bonded to each of said layers by a surface reaction product between the layer and the adjacent organic acid.

3. An effervescent granulate according to claim 1 wherein one of said layers also contains sodium or potassium bicarbonate or both.

4. An effervescent granulate according to claim 1 which also includes at least one distinct layer consisting essentially of a sodium or potassium salt.

5. An effervescent granulate according to claim 4 which includes a layer of potassium bicarbonate overlying a calcium carbonate layer.

6. An effervescent granulate according to claim 1 wherein said bonding layer covers at least 80% of the surface of said organic acid crystals.

7. An effervescent granulate according to claim 6 wherein said bonding layer covers at least 95% of the surface of said organic acid crystals.

8. An effervescent granulate according to claim 1 wherein the grain size of the calcium carbonate is about one order of magnitude smaller than that of said organic acid crystals.

9. An effervescent granulate according to claim 1 wherein said bonding layer adjacent to a calcium carbonate layer contains a maximum of 5% by weight of calcium carbonate.

10. An effervescent granulate according to claim 9 wherein said bonding layer adjacent to a calcium carbonate layer contains a maximum of 2% by weight of calcium carbonate.

11. An effervescent granulate according to claim 1 wherein the calcium carbonate has a particle size not in excess of 20 microns.

12. A method for the manufacture of an effervescent granulate which comprises moistening particles of a crystalline edible organic acid with a solvent for said acid,
mixing the moistened acid particles under agitation with solid, powdery calcium carbonate under conditions sufficient to produce a surface reaction between said acid crystals and said calcium carbonate and the formation of a generated calcium carbonate layer upon the crystals with the elimination of reaction water,
adding additional crystalline organic acid and agitating the same with the surface-reacted particles to react with the generated calcium carbonate layer while the same is still damp with said reaction water,
adding calcium carbonate or an alkali bicarbonate to the particles thus treated to react with the remaining additional crystalline organic acid,
repeating the steps of adding crystalline organic acid and calcium carbonate or alkali bicarbonate until the desired number of additional layers has been built up and
applying a vacuum to terminate further layer formation.

13. A method according to claim 12 wherein said crystalline edible organic acid is adipic acid, malic acid, ascorbic acid, fumaric acid, or citric acid.

14. A method for the manufacture of an effervescent granulate which comprises:
providing citric acid particles of a grain size between 50 and 700 microns,
applying a vacuum to said particles to bring the ambient pressure to at least as low as 0.1 bar,
moistening said particles with a mixture of alcohol and water while at a temperature of about 40° C. to 60° C.,
adding calcium carbonate particles having a grain size substantially less than the grain size of said citric acid particles to form a mixture comprising a layer of calcium carbonate over said citric acid particles,
agitating said mixture while increasing the pressure thereon to the range of 800 to 900 mbar, and
drying said mixture at a pressure of about 10 to 20 mbar.

15. A method according to claim 14 wherein said mixture of alcohol and water contains 50 to 70 weight % alcohol, and the weight ratio of citric acid to alcohol to calcium carbonate is 0.013 to 0.385 parts by weight alcohol, and 0.085 to 0.042 parts by weight calcium carbonate per one part by weight of citric acid.

16. A method according to claim 14 wherein after the step of increasing the pressure, additional citric acid particles are again added and reacted with the calcium carbonate present on the citric acid particles utilizing the water generated in the preceding reaction between said calcium carbonate and citric acid.

17. A method according to claim 14 wherein at least two calcium carbonate layers are deposited, followed by deposition of a sodium or potassium salt.

18. A method according to claim 14 which includes the step of applying a layer of potassium bicarbonate over said calcium carbonate layer.

19. A method according to claim 12 wherein the calcium carbonate has a grain size not in excess of 20 microns.

20. An effervescent tablet produced from the granulate of claim 1.

21. A method for the manufacture of an effervescent mixture which comprises:
mixing together a crystalline organic acid, a carbonate, alcohol and water at a pressure of up to 0.1 bar,
applying calcium carbonate to the resulting mixture, and
reacting the added calcium carbonate with the moistened surfaces of the organic acid crystals until the pressure due to $CO_2$ evolution during the reaction causes the pressure to rise to about 0.9 bar.

22. A method according to claim 14 which includes the steps of:
adding additional quantities of calcium carbonate together with potassium bicarbonate and additional quantities of alcohol and water after the initial reaction with $CaCO_3$, and reacting the additional $CaCO_3$ with the previously reacted crystals.

23. A method according to claim 14 which includes the steps of:
drying the coated and reacted crystals, and
coating the dried crystals with fumaric acid.

24. An effervescent granulate according to claim 1 wherein at least one layer contains a water insoluble calcium salt additive.

25. An effervescent granulate according to claim 1 wherein at least one layer contains calcium gluconate.

26. An effervescent granulate according to claim 1 wherein at least one layer contains magnesium oxide.

27. An effervescent granulate according to claim 1 wherein at least one layer contains a vitamin complex of the B group.

28. An effervescent granulate according to claim 24 wherein at least one layer contains a mixture of calcium carbonate and water-free starch.

29. An effervescent granulate according to claim 24 wherein at least one layer contains a mixture of calcium carbonate and calcium levulinate.

30. An effervescent granulate according to claim 24 wherein at least one layer contains a mixture of calcium carbonate and iron sulfate.

31. An effervescent granulate according to claim 1 in which at least one layer contains a water insoluble calcium salt additive and water-free starch, said starch being present in an amount of from 2 to 8% by weight of the calcium carbonate present.

32. An effervescent granulate according to claim 1 wherein said organic acid crystals are citric acid crystals of different grain sizes, one grain size lying in the range of 0.4 to 0.6 mm and the other being on the order of 0.1 mm.

* * * * *